United States Patent [19]

Morkun et al.

[11] Patent Number: 5,078,011

[45] Date of Patent: Jan. 7, 1992

[54] METHOD OF MONITORING PARAMETERS OF SOLID PHASE OF SUSPENSION AND DEVICE THEREFOR

[75] Inventors: Vladimir S. Morkun; Viktor N. Potapov, both of Krivoi Rog, U.S.S.R.

[73] Assignee: Krivorozhsky Gornorudny Institut, Krivoi Rog, U.S.S.R.

[21] Appl. No.: 449,856

[22] PCT Filed: Apr. 25, 1988

[86] PCT No.: PCT/SU88/00098

§ 371 Date: Dec. 13, 1989

§ 102(e) Date: Dec. 13, 1989

[87] PCT Pub. No.: WO89/10559

PCT Pub. Date: Nov. 2, 1989

[51] Int. Cl.[5] .................... G01N 9/24; G01N 29/20
[52] U.S. Cl. ........................... 73/599; 73/601; 73/61 R; 73/32 A
[58] Field of Search ............... 73/61 R, 61.1 R, 601, 73/599, 32 A, 19

[56] References Cited

U.S. PATENT DOCUMENTS

| 4,237,720 | 12/1980 | Abts | 73/53 |
| 4,381,674 | 5/1983 | Abts | 73/599 |
| 4,412,451 | 11/1983 | Uusitalo et al. | 73/865.5 |
| 4,667,515 | 5/1987 | Farren et al. | 73/601 |
| 4,683,759 | 8/1987 | Skarsuaag et al. | 73/61.1 R |

FOREIGN PATENT DOCUMENTS

| 3407465 | 8/1985 | Fed. Rep. of Germany . |
| 55-2581 | 1/1980 | Japan . |
| 59-47259 | 11/1984 | Japan . |
| 58-41336 | 3/1985 | Japan . |
| 275499 | 10/1970 | U.S.S.R. . |
| 714270 | 2/1980 | U.S.S.R. . |
| 896542 | 1/1982 | U.S.S.R. . |
| 1231453 | 5/1986 | U.S.S.R. | 73/61 R |

OTHER PUBLICATIONS

"Oprobovanie i kontrol tekhnologicheskikh protsessov obogascheniya", 1979, Nedra Publ., Moscow, pp. 47-49 (partial translation).

Primary Examiner—Hezron E. Williams
Assistant Examiner—Rose M. Finley
Attorney, Agent, or Firm—Fleit, Jacobson, Cohn, Price, Holman & Stern

[57] ABSTRACT

This invention relates to measurements of characteristics of a comminuted material by an ultrasonic method. The method of monitoring parameters of a solid phase of suspension comprises the steps of producing a Lamb wave and gamma-radiation and passing them respectively through a test medium (2) along the wall of a measuring vessel (1) and through the test medium (2) placed therein, measuring the amplitude of the Lamb wave and the intensity of gamma-radiation, while using, as the test medium, separately a standard liquid and the analyzed suspension to find the parameters of the solid phase of suspension by way of the ratio of the measured values. A device realizing this method comprises a measuring vessel (1), an emitting ultrasonic converter (4), a receiving ultrasonic converter (7) which are mounted on the wall of the measuring vessel (1) separated by forming prisms (5 and 6), a pulse generator (3), amplifiers (8 and 18), a source (16) of gamma-radiation and a receiver (17) of gamma-radiation which are mounted on the walls of the measuring vessel (1), a multivibrator (9), a one-shot multivibrator (10), a delay line (11), a square pulse generator (12), a gating unit (13), smoothing filters (14, 19), an amplitude detector (15), and a data processing assembly (20) comprising units (21 and 22) for setting standard values, two subtraction circuits (23, 24) and a dividing circuit (25).

2 Claims, 2 Drawing Sheets

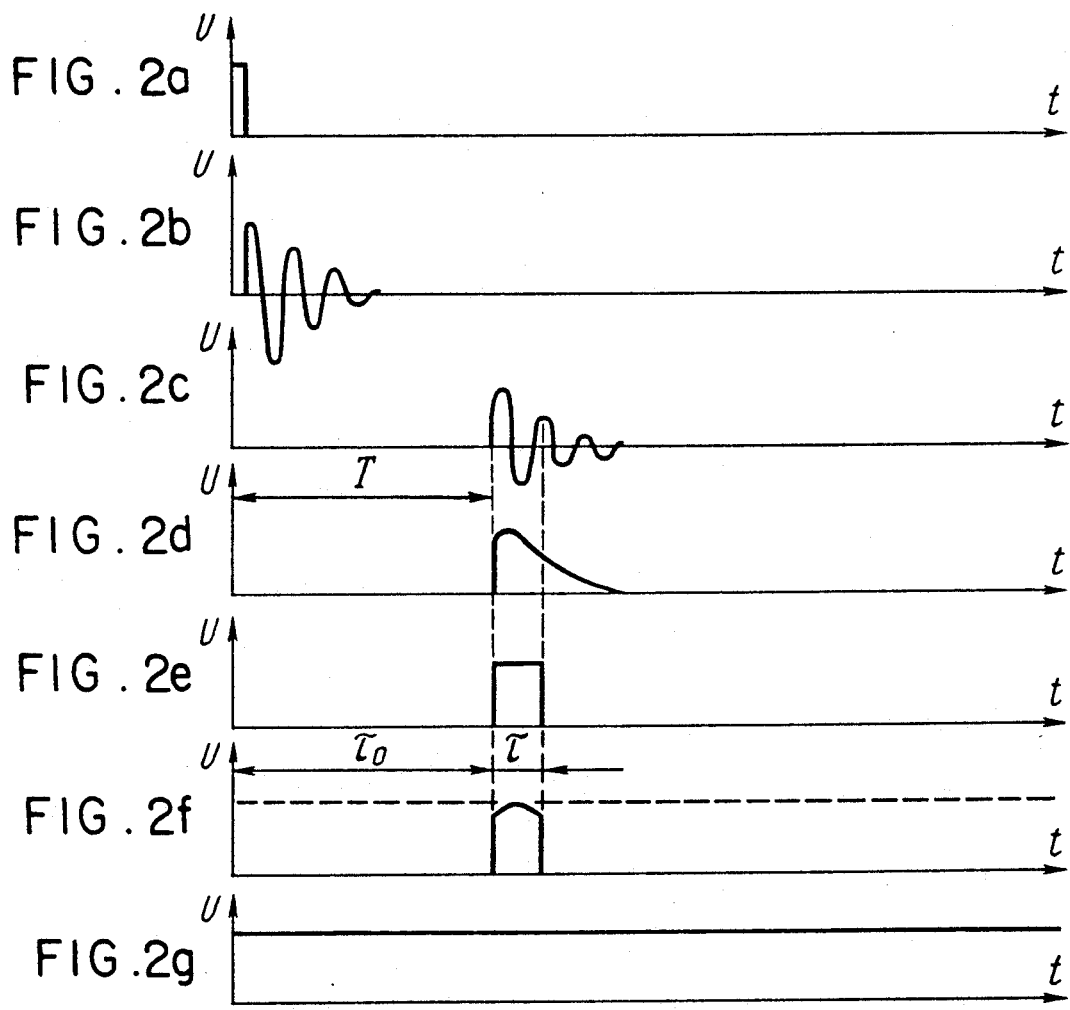

METHOD OF MONITORING PARAMETERS OF SOLID PHASE OF SUSPENSION AND DEVICE THEREFOR

TECHNICAL FIELD

This invention relates to methods of measuring characteristics of comminuted materials in a liquid medium by ultrasonic methods and, in particular, to a method of monitoring parameters of a solid phase of suspension and a device realizing this method.

BACKGROUND ART

There is a known method for monitoring parameters of a solid phase of suspension (cf., G. A. Han "Oprobovanie i kontrol tekhnologicheskikh protsessov obogascheniya", 1979, Nedra Publ., Moscow, pp. 47–49) which comprises the steps of preliminarily forming a sample of suspension to be analyzed, obtaining a solid phase of the formed suspension sample, for example, by drying, and measuring mass and subsequently volume thereof. The sample volume is determined considering a change in the volume of the liquid displaced as the dry material constituting the solid phase of the formed sample is immersed in a measuring vessel containing the liquid. The density of particles in the solid state of the analyzed suspension is determined by the relation between the measured mass of the solid phase of the formed suspension and the volume thereof.

There is also known a method of monitoring parameters of a solid phase of suspension (cf.SU, A, 896,542) wherein ultrasonic vibrations are set up at several fixed frequencies and applied to a test medium placed in a measuring vessel. The ultrasonic vibrations are affected by the test medium whereby parameters of said vibrations, more specifically, their amplitude change are monitored. In this case the text medium is a mixture of particles in the solid state of the analyzed suspension and liquid, for example, clean water. Thereafter, the amplitude of the ultrasonic vibrations passed through the test medium is measured, the value thereof being used to determine the size of particles in the analyzed suspension. Also, measurements are made of the time at which particles of a definite size settle within the measuring vessel. The time value is used to determine the density of particles of the analyzed suspension.

There is also known a device for accomplishing the foregoing method of monitoring parameters of a solid phase of suspension (SU, A, 896,542), which comprises such series-connected components as a pulse generator and an emitting ultrasonic converter, and also a receiving ultrasonic converter connected to the input of an amplifier designed to amplify an ultrasonic vibration amplitude signal. The emitting ultrasonic converter and the receiving ultrasonic converter are disposed on a wall of a measuring vessel on different sides thereof and are acoustically interconnected via the test medium. The measuring vessel is filled with the test medium representing a mixture of solid particles of the analyzed suspension and clean water. The known device also includes a data-processing assembly designed to determine parameters of the analyzed suspension using the results obtained in amplitude measurements. The received data is in turn used for computing parameters of the solid phase of said suspension, said data-processing assembly comprising a standard-amplitude setting unit and a subtraction circuit. The input of the data-processing assembly is connected to the output of the amplifier so that, in the given case, the quantity measured is the amplitude of ultrasonic vibrations dying out when passed through the test medium.

In the afore-mentioned device the test medium placed in the measuring vessel passes ultrasonic vibrations at several fixed frequencies, said vibrations being produced by the use of the pulse generators and the emitting ultrasonic converters. As stated above, the test medium represents particles in the solid state of the suspension taken for analysis from the production line, said particles being immersed in clean water contained in the measuring vessel.

The receiving ultrasonic converters convert ultrasonic vibrations passed through the test medium into electrical signals that characterize the amplitude of said ultrasonic vibrations and are amplified by the amplifier. The measured amplitudes of the amplifier output signals are used to determine parameters of particles in the solid phase of the analyzed suspension. The amplitudes of the amplifier output signals are measured at fixed time intervals after said particles in the solid phase begin to settle, the counting being started immediately after their immersion in clean water contained in the measuring vessel. The obtained data is used to determine the size of solid particles and the density of the solid phase of the analyzed suspension.

However, the prior art methods of monitoring parameters of a solid phase of suspension, which have been discussed above, and the device therefor are characterized by a long checking process inasmuch as parameters of a solid state of suspension are measured as a function of precipitation over a long time in a series of tests performed on a stationary test medium at predetermined time intervals.

Before checking, it is necessary to remove the solid phase and dry it as a preparatory step. Such operations involve losses of suspended particles during preparation and transfer of samples, a disadvantage substantially decreasing checking accuracy. Moreover, accuracy in measuring parameters of a solid phase of suspension with an ultrasonic wave passed throughout a test medium is appreciably decreased due to a varying size of solid-phase particles, which is also a limiting factor.

DISCLOSURE OF THE INVENTION

The object of this invention is to provide a method of monitoring parameters of a solid phase of suspension and a device realizing this method, which would permit continuous monitoring of parameters of a solid phase of suspension during the movement of a test medium without such preliminary steps as removal and preparation of a solid phase of suspension with a view to improving the accuracy of measurements and reducing the total monitoring time.

There is provided a method of monitoring parameters of a solid phase of suspension, comprising the steps of forming and emitting an ultrasonic vibration, passing it through a test medium placed in a measuring vessel, subsequently measuring the amplitude of the ultrasonic vibration passed through the test medium and using the obtained amplitude values for determining parameters of the test medium, in which, according to the invention, a standard liquid of suspension is separately used as the test medium, gamma radiation is additionally formed and successively passed through said standard liquid and suspension, a measurement is made of intensity of said gamma radiation passed through said standard liquid and suspension, a Lamb wave being used as said ultrasonic vibration, said wave being propagated in said standard liquid and suspension along a wall of the measuring vessel whereupon a measurement is made of the amplitude of the Lamb wave passed along said wall of the measuring vessel over a fixed distance, while parameters of the solid phase of the suspension are determined using the relation between the obtained values of the Lamb wave amplitude and the intensity of said gamma radiation.

It is preferable that the hereinproposed method of monitoring parameters of a solid phase of suspension should comprise the steps of additionally forming ultrasonic vibrations and applying them to said standard liquid and the analyzed suspension before said gamma radiation is propagated.

There is also provided a device for accomplishing the hereinproposed method of monitoring parameters of a solid phase of suspension, comprising a measuring vessel, an emitting ultrasonic converter, a receiving ultrasonic converter, said converters being disposed on a wall of the measuring vessel, a pulse generator connected to the input of the emitting ultrasonic converter, a first amplifier connected to the output of the receiving ultrasonic converter, and a data-processing assembly connected to the output of the first amplifier, which, according to the invention, comprises a multivibrator, a one-shot multivibrator, a delay line, a square pulse shaper, a gating unit, and a first smoothing filter, said components being connected in series, an amplitude detector having its input connected to the output of the first amplifier and its output connected to a data in-out of the gating unit, a gamma radiation source and a gamma radiation receiver, which are disposed on opposite walls of the measuring vessel, a second amplifier and a second smoothing filter whose input is connected to the output of the gamma radiation receiver via the second amplifier, the amplifiers used being logarithmic amplifiers, acoustically interconnected receiving and emitting ultrasonic converters being disposed on a wall on the measuring vessel at a predetermined distance from each other with forming prisms therebetween, the data-processing assembly comprising two units for setting standard values of the Lamb wave amplitude and the gamma radiation intensity, two substraction circuits and a dividing circuit, the outputs of the standard-value setting units being respectively connected to the inputs of the subtraction circuits, the outputs of which are connected to the inputs of the dividing circuit and whose inputs are connected to the outputs of the smoothing filters.

It is of advantage that the device should comprise an additional pulse generator and an additional emitting ultrasonic converter connected via its input to the output of the additional pulse generator whose input is connected to the output of the one-shot multivibrator, provision being also made for a storing vessel hydraulically connected with the measuring vessel and having connections for delivering and draining a test medium, the additional emitting ultrasonic converter being arranged within the storing vessel.

The invention makes it possible to reduce the time required for checking parameters of a solid phase of suspension and to enhance accuracy of their measurement due to: omission of such a preliminary step as preparation of a test sample of said suspension; utilization of Lamb waves propagated in the test medium along a wall of the measuring vessel; and employment of additional influencing factors, more specifically, gamma radiation and additional ultrasonic vibrations, an advantage appreciably decreasing the effect of gas pockets and a varying size of particles of the solid phase of said suspension in measurements of the Lamb wave amplitude and the gamma radiation intensity.

Furthermore, solid-phase parameters are checked in a moving test medium, that is, while the analyzed suspension and standard liquid are in flow, a factor decreasing the duration of the checking process and making the obtained data more reliable.

Also, the test area will be free of gas pockets due to the utilization of additional ultrasonic vibrations and provision of a storing vessel with an additional emitting converter and an additional pulse generator, a feature enhancing accuracy in measuring parameters of a solid phase of suspension.

BRIEF DESCRIPTION OF DRAWINGS

These, together with other objects and features of the invention will become more readily apparent from the following detailed description with reference to a specific embodiment thereof, taken in conjunction with the accompanying drawings, wherein:

FIGS. 2a–2g are diagrams illustrating operation of the device of FIG. 1 according to the invention.

BEST MODE OF CARRYING OUT THE INVENTION

Figure 1:
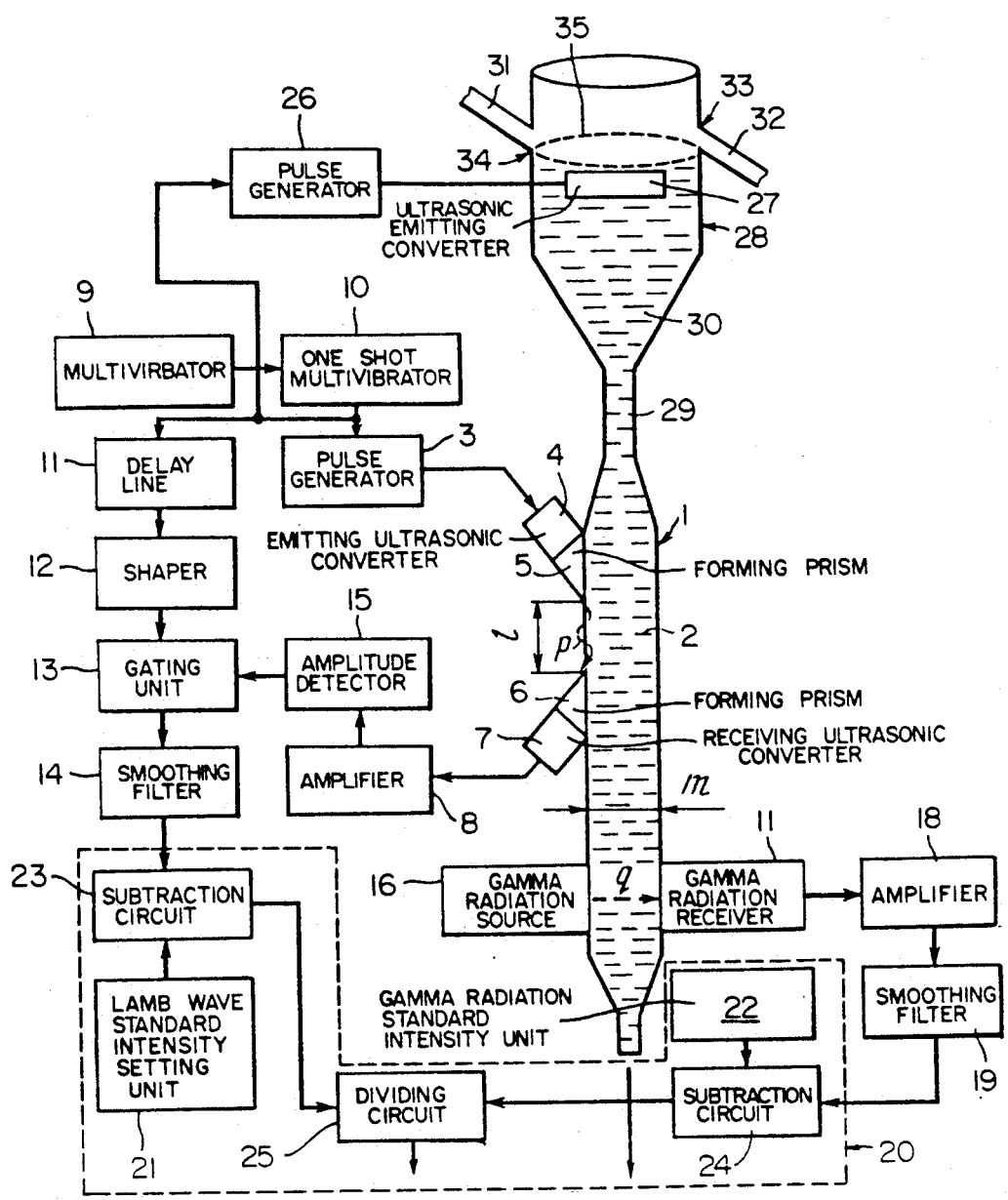
FIG. 1 is a block diagram of a device for accomplishing a method of monitoring parameters of a solid phase of suspension according to the invention.

The method of monitoring parameters of a solid phase of suspension forming the subject of the present invention is accomplished as follows. A pump (not shown in the drawing) is continuously operated to fill a measuring vessel 1 (FIG. 1) with a test medium 2 which is initially a standard liquid, for example, clean water. Simultaneously an ultrasonic vibration is produced and transformed into a Lamb wave, which is generated in a wall of the measuring vessel 1, and an additional influencing factor (gamma radiation) is provided. The Lamb wave propagates at the interface between the measuring vessel 1 and the test medium 2, that is, along the wall of the measuring vessel 1, as shown with arrow "p", while said gamma radiation is transmitted transversely through the test medium 2, as shown with arrow "q".

After the Lamb wave covers a fixed distance "l" on the wall of the measuring vessel 1, it is converted into an ultrasonic vibration and then into an electrical signal whose amplitude is amplified on a logarithmic scale, which ends the process of obtaining a signal characterizing the amplitude of the Lamb wave affected by the standard liquid. Thereafter the signals amplified on a logarithmic scale are detected and a low-frequency component is derived, which completes the process of measuring the Lamb wave amplitude for the standard liquid, the measured value being a standard amplitude of the Lamb wave.

After the gamma radiation covers a fixed distance "m" in the test medium 2, the glow originated by said gamma radiation is converted into an electrical signal, its amplitude being amplified on a logarithmic scale, said signal characterizing the intensity of the gamma radiation affected by the test medium 2, that is, by the standard liquid. This signal is frequency-averaged, which ends the process of measuring the gamma radiation intensity for the standard liquid, the measured value being a standard intensity of the gamma radiation. Next, the standard liquid is drained and the measuring vessel is again filled with the test medium 2 which is now a suspension whose solid phase consists of particles measuring about 1 mm. The suspension possesses sufficient fluidity since its solid phase is mixed with a suitable liquid. The above process of measuring the Lamb wave amplitude and the gamma radiation intensity is repeated this time for the suspension (hereinafter referred to as "effective value").

The measured values of the Lamb wave amplitude and the gamma radiation intensity for the standard liquid and the suspension are used to determine concentration and density of the solid phase of said suspension by calculating a logarithmic difference between the Lamb wave amplitudes for the standard liquid and the suspension and also a logarithmic difference between the gamma radiation intensities for the standard liquid and the suspension whereupon the relation between said differences is determined. The ultrasonic vibration frequency range is preferably within 400 kHz–3.5 MHz. The gamma radiation intensity varies within wide limits, a condition attainable by the use of any standard sources thereof.

A detailed description of the proposed method for monitoring parameters of a solid phase of suspension will now be continued by reference to a preferred embodiment of the device therefore, which comprises the measuring vessel 1 designed to accommodate the test medium 2, that is, the standard liquid or the analyzed suspension. The device forming the subject of the present invention also comprises a pulse generator 3 whose output is connected to an emitting ultrasonic converter 4 disposed on a wall of the measuring vessel 1 via a forming prism 5 intended for converting ultrasonic vibrations coming from the output of the emitting ultrasonic converter 4 into a Lamb wave propagating along the wall of the measuring vessel 1 at the interface between said wall and the test medium 2, as shown with arrow "p". A receiving ultrasonic converter 7 is arranged at a fixed distance "1" from the forming prism 5 within an acoustic communication area by the use of another forming prism 6, the output of said converter being connected to the input of an amplifier 8 serving to amplify the signal characterizing the Lamb wave amplitude. The forming prism 6 and the receiving ultrasonic converter 7 are designed to conver the Lamb wave into ultrasonic vibrations and into a corresponding electrical signal.

The device also includes sich series-connected components as a multivibrator 9, a one-shot multivibrator 10, a delay line 11, a square pulse shaper 12, a gating unit 23, and a first smoothing filter 14 designed to obtain a signal representative of the Lamb wave amplitude. The data input of the gating unit 13 is connected to the output of an amplitude detector 15 having its input connected to the output of the amplifier 8, while the input of the pulse generator 3 is connected to the output of the one-shot multivibrator 10. The hereinproposed device also comprehends a gamma radiation source 16 and a gamma radiation receiver 17 arranged oppositely on different sides of the measuring vessel 1 (in a cross-section) and separated by a fixed distance "m" equal to the width of the measuring vessel 1. The output of the gamma radiation receiver 17 is connected to the input of an amplifier 18 used to amplify the amplitude of the signal characterizing the gamma radiation intensity. The components 18 and 8 are logarithmic amplifiers, and the gamma radiation receiver 17 is a scintillator connected to a photomultiplier (not shown in FIG. 1). The output of the amplifier 18 is connected to the input of a second smoothing filter 19. The outputs of the smoothing filters 14 and 19 are connected to the inputs of a data-processing assembly 20 used to process the measured values of the Lamb wave amplitude and the gamma radiation intensity for the standard liquid and the analyzed suspension, said values being represented in an analog or digital form. The processing is aimed at obtaining the required parameters of the solid phase of the suspension, that is, its density and concentration. The data-processing assembly 20 comprises a Lamb wavestandard amplitude setting unit 21 and a gamma radiation standard intensity setting unit 22. The output of each of said units 21 and 22 is connected to one of the inputs of subtraction circuits 23 and 24, respectively. The other input of each of said subtraction circuits 23 and 24 acts as one of the inputs of the data-processing assembly 20 connected, respectively, to the output of the smoothing filter 14 and to the output of the smoothing filter 19. The output of each of said subtraction circuits 23 and 24 is connected to a respective input of a dividing circuit 25 whose output serves as the output of the device, providing a signal representative of the density of the solid phase of the suspension. A signal representative of the concentration of the solid phase of the suspension is derived from the output of the subtraction circuit 23.

The device forming the subject of the invention also incorporates an additional pulse generator 26 connected via its input to the output of the one-shot multivibrator 10 and via its output to the input of an additional ultrasonic emitting converter 27 providing high-power ultrasonic vibrations for eliminating the effect of gas pockets in the test medium 2, a feature enhancing measuring accuracy. The additional ultrasonic converter 27 is arranged within a storing vessel 28 hydraulically linked with the measuring vessel 1 through a connection 29 communicating via an adapter funnel 30 with the storing vessel 28 which is a cylindrical structure in the preferred embodiment of the invention. The storing vessel 28 has connections 31 and 32 for delivering and draining the test medium 2, respectively. The drain connection 32 is in communication with the cavity of the storing vessel 28 via an outlet 33 provided in the wall of the storing vessel 28 above the additional emitting ultrasonic converter 27 and below an inlet 34 so that the ultrasonic converter 27 is always found below a level 35 of the test medium 2 in the storing vessel 28.

The emitting ultrasonic converter 4 and the receiving ultrasonic converter 7 use known circuitry (cf. V. V. Malov, "Piezorezonansnye datchiki", 1978, Energy publishers, Moscow, p. 37).

The generator 3 and the additional pulse generator 26 may be constructed in a known manner (for example, as described in "Impulsnaya tekhnika" by Yu. A. Brammer et al., Vischaya Shkola publishers, 1976, Moscow, p. 136). Refer to the same publication for the construction of the gating unit 15 (p. 305) and the smoothing filters 14 and 19 (p. 150).

The units 21, 22, the substraction circuits 23, 24 and the dividing circuit 25 are essentially similar to known components (cf. V. I. Korneychuk et al. "Vychislitelnye ustroistva na mikroskhemakh", 1986, Technika publishers, Kiev).

The gamma radiation source 16 is a stock-produced unit providing gamma radiation with intensity varying within wide limits (cf. G. A. Khan, "Cheking and monitoring of concentration processes", 1979, Nedra publishers, Moscow).

Turning now to FIGS. 2a-2g there are shown voltage waveforms at different points of the circuitry illustrating operation of the device in compliance with the invention. In the drawing voltage U is plotted in the ordinate and time t on the abscissa. FIG. 2a shows the output signal of the one-shot multi-vibrator 10; FIG. 2b, the output signal of the pulse generator 3; FIG. 2c, the output signal of the amplifier 8; FIG. 2d, the output pulse of the amplitude detector 15; FIG. 2e, the output pulse of the shaper 12; FIG. 2f, the output signal of the gating unit 13; and FIG. 2g, the output signal of the smoothing filter 14.

The device for carrying out the proposed method of monitoring parameters of a solid phase of suspension operates in the following manner.

The test medium 2, which is a standard liquid in the case under discussion, flows through the storing vessel 28 and the measuring vessel 1.

The multivibrator 9 furnishes square pulses which are used to trigger (FIG. 2a) the pulse generator 3 (FIG. 1) by means of the one-shot multivibrator 10. The pulse generator 3 induces a series of high-frequency electrical oscillations at a fixed frequency (FIG. 2b). (FIG. 2 illustrates conversion of one pulse).

The emitting ultrasonic converter 4, for example, of piezoelectric type converts an electrical signal derived from the output of the generator 3 into elastic ultrasonic vibrations of the test medium 2 with which it is in contact. Said ultrasonic vibrations are transformed by the forming prism 5 into Lamb waves propagating along the wall of the measuring vessel 1 containing the test medium 2. After covering the fixed distance "1" on the wall of the measuring vessel 1, the Lamb waves come to the other forming prism 6 which transforms them into longitudinal ultrasonic vibrations, said vibrations being subsequently transmitted to the receiving ultrasonic converter 7. The receiving ultrasonic converter 7 converts the longitudinal ultrasonic vibrations into an electrical signal. As the Lamb waves pass the fixed distance "1" on the wall of the measuring vessel 1 containing the test medium 2, their damping is governed solely by concentration of the solid phase of the suspension and depends neither in the particle size nor on the size spread.

Simultaneously a pulse from the one-shot multivibrator 10 is applied to the input of the delay line 11. From the delay line 11 it comes to the shaper 12 generating a square pulse (FIG. 2e) which enables the gating unit 13. Delay time $\tau_o$ of the pulse delivered to the shaper 12 through the delay line 11 is dependent upon time T (FIG. 2c) during which the pulse furnished by the pulse generator 3 is delivered from the emitting ultrasonic converter 4 to the receiving ultrasonic converter 7. Duration $\tau$ of the square pulse generated by the shaper 12 (FIG. 2e) corresponds to the duration of the data-carrying portion of the received signal appearing at the output of the amplifier 8 (FIG. 2c) after the time T. In this case $T = \tau_o$.

The signal received by the receiving ultrasonic converter 7 is amplified on a logarithmic scale by the amplifier 8 (FIG. 2c) and detected by the amplitude detector 15 from which the signal (FIG. 2d) is applied to the gating unit 13 which passes only the data-carrying portion of the received signal (FIG. 2f), while the smoothing filter 14 separates a low-frequency component therefrom, that is, converts the pulse signal into a direct-current signal of the same amplitude (FIG. 2g), said amplitude corresponding to that of the Lamb wave passed along the wall of the measuring vessel 1.

The setting unit 21 is adjusted for a standard amplitude $S_{\lambda o}$ of the signal obtained on passing the Lamb wave as the standard liquid flows in the measuring vessel 1.

The gamma radiation source 16 sets up gamma radiation propagated through the walls of the measuring vessel 1 and the test medium 2, that is, through the standard liquid. Under the effect of the gamma radiation a flash occurs in the scintillator of the receiver 17. The resultant glow is intensified and converted into electrical current by the photomultiplier of the receiver 17. The amplifier 18 is used to find the logarithm of the amplitude of the signal derived from the output of the receiver 17, while the smoothing filter 19 separates a low-frequency component of the amplified signal.

The setting unit 22 sets the signal amplitude $S_{\gamma o}$ corresponding to the intensity of the recorded gamma radiation with the standard liquid present in the measuring vessel 1, that is, to the standard intensity of the gamma radiation.

The standard liquid is subsequently drained and the measuring vessel 1 is filled with the suspension to be analyzed. Thereafter the pulse generator 3 and the gamma radiation source 16 are turned on and the above operations are performed on the test medium 2 which is now the suspension. The damping of the gamma radiation is governed solely by the concentration of the solid phase of the suspension and by the density of its particles and does not depend on the size of said particles. As a result, measurements are made of the Lamb wave amplitude and the gamma radiation intensity for the suspension, that is, of the effective values of $S_\lambda$ and $S_\gamma$.

The inputs of the subtraction circuit 23 accept signals from the output of the unit 21 and the smoothing filter 14, that is $S_{\lambda o}$ and $S_\lambda$, the difference therebetween being determined by said circuit. The computed difference $S_{\lambda o} - S_\lambda$ corresponds to the concentration of the solid phase in the analyzed medium and may be represented in any form (analog or digital).

The substraction circuit (24) computes the difference between $S_{\gamma o}$ and $S_\gamma$, which corresponds to the gamma radiation intensity and depends both on the concentration and density of the solid phase of the suspension, that is, the computed difference is $S_{\gamma o} - S_\gamma$.

The dividing circuit 25 computes the magnitude $$S = \frac{S_{\gamma o} - S_\gamma}{S_{\lambda o} - S_\lambda},$$

which corresponds to the density of particles in the solid phase of the analyzed suspension.

To eliminate the effect of gas pockets on the results obtained in measuring the magnitude S, the pulses from the one-shot multivibrator 10 are used to trigger the additional generator 26, thereby inducing high-power ultrasonic vibrations whose dynamic effects (acoustic flow and radiation pressure) are utilized to degas the test medium 2. Stated differently, the gas phase (gas pockets and bubbles) are removed from the test medium 2 contained in the storing vessel 28. The effect of the gas medium upon the gamma radiation intensity is, thus, prevented.

The constant level 35 of the test medium 2 over the additional emitting ultrasonic converter 27 and its stable flow through the measuring vessel 1 are the necessary conditions for adequate degassing of the test medium 2 and measurements of its parameters in the measuring vessel 1 with minimum errors. Therefore, the amount of the test medium 2 supplied to the storing vessel 28 through the connection 31 exceeds that drained through the connection 32. The excessive amount is discharged through the connection 32, that is, the constant level 35 of the suspension or standard liquid is maintained in the storing vessel 28.

To decrease variation of the level of the test medium 2 in the storing vessel 28, it is fed thereto through the connection 31 which is disposed above the connection 32. The incoming test medium 2 is set in rotary motion about the centre of the storing vessel 28 with minimum oscillations of its surface without segregation of particles of the solid phase, while its excessive amount is discharged through the connection 32. Such an arrangement of the connection 32 provides for minimum variations of the level of the test medium 2 when it is drained.

EXAMPLE 1

The parameters of a solid phase of suspension were checked in compliance with the method forming the subject of the present invention. The output pulses of the generator 3 had the following parameters: duration, 5 $\mu$s; amplitude, 180 V; recurrence rate, 1000 Hz. The gamma radiation source 16 was one having cobalt isotope $Co^{60}$ as an active element. The analyzed suspension was ferromagnetite. The density of the solid phase of the suspension corresponding to the measured value of the output signal of the dividing circuit 25 (4.1 V) was found to be 3.2 g/cm$^3$.

EXAMPLE 2

The parameters of the output pulses of the generator 3 were similar to those given in Example 1 above. The gamma radiation source 16 was one having caesium isotope $Cs^{137}$ as an active element. The analyzed suspension was copper-containing ore. The density of the solid phase of the suspension corresponding to the measured value of the output signal of the dividing circuit 25 (3.5 V) was found to be 2.9 g/cm$^3$.

As is apparent from the above description of the proposed method for monitoring density of a solid phase of suspension and the device therefor, an advantage of the present invention is that it eliminates a preliminary step of preparing a sample of suspension to be analyzed, that is, there is no need to separate and dry the solid phase inasmuch as the checking process is effected continuously in the flowing test medium 2, for example, in the flowing suspension or standard liquid. This advantage is attributed to the utilization of a new factor affecting a test medium, that is, gamma radiation whose intensity is governed solely by the concentration and density of a solid phase of suspension and depends neither on a particle size spread nor on the effect of gas bubbles occurring in the test medium 2. The use of a Lamb wave as an ultrasonic wave propagating on the wall of the measuring vessel permits checking density of the solid phase of the suspension at the interface between the wall and the test medium, a factor making measurements less dependent on a particle size spread and on the effect of gas bubbles. The device forming the subject of the present invention comprises special forming prisms 5 and 6 transforming ultrasonic vibrations into a Lamb wave and vice versa, as well as the gamma radiation source 16 and the gamma radiation receiver 17 incorporating a scintillator and a photomultiplier. Furthermore, such components of the device as the multivibrator 9, the one-shot multivibrator 10, the delay line 11, the square pulse shaper 12, the gating unit 13, the amplitude detector 15, the smoothing filters 14, 19 and the amplifiers 8, 18 provide for matched operation of the emitting and receiving ultrasonic converters 4, 7 of the device and its gamma radiation source 16 and receiver 17 in accordance with the operations comprised in the proposed method of monitoring density of the solid phase of the suspension. The preferred circuitry of the data-processing assembly 20 with the logarithmic amplifiers 8 and 18 makes it possible to compute both density of the solid phase of the analyzed suspension and its concentration (the output signal of the unit 23). All the positive features mentioned above permit decreasing the duration of a parameter monitoring process and enhancing measuring accuracy. The accuracy of measurements may also be improved if, before transmitting gamma radiation and a Lamb wave through the test medium 2, according to the present method of monitoring parameters of a solid phase of suspension, said test medium 2 is additionally subjected to a high-power ultrasonic vibrations, which is done by incorporating, in the circuitry of the device, an additional pulse generator 26 and an additional emitting ultrasonic converter 27 arranged within the storing vessel 28, hydraulically linked with the measuring vessel 1, below the level 35 of the test medium 2. This procedure eliminates gas pockets in the test medium 2 which might cause errors in measurements of intensity of gamma radiation transmitted through the test medium 2.

INDUSTRIAL APPLICABILITY

This invention can be used in ore-mining, chemical and construction industries for measuring concentrations and density of particles in a solid phase of gas-containing suspensions, which is required to effect further control over the concentration process of, for example, ore rocks.

We claim:

1. A device for monitoring parameters of a solid phase of suspension, comprising a measuring vessel, an emitting ultrasonic converter mounted on a wall of the measuring vessel for passing Lamb waves along said wall, a receiving ultrasonic converter mounted on said wall of the measuring vessel a fixed distance from the emitting ultrasonic converter, a generator of Lamb waves, connected to an input of the emitting ultrasonic converter, an amplifier of an ultrasonic vibration signal, connected to an output of the receiving ultrasonic converter, and a data processing assembly electrically connected with the amplifier and including in sequence a multivibrator, a one-shot multivibrator, a delay line, a square pulse shaper, a gating unit, and a smoothing filter, all connected in series, an amplitude detector having an output connected to a data input of the gating unit, a gamma-radiation source and a gamma-radiation receiver mounted on the walls of the measuring vessel opposite each other, a gamma-radiation signal amplifier and another smoothing filter with an input connected via the gamma-radiation signal amplifier to the output of the gamma-radiation receiver, and wherein the amplifiers are logarithmic amplifiers, while the receiving ultrasonic converter and the emitting ultrasonic converter are acoustically coupled to each other and mounted on the wall of the measuring vessel via forming prisms at a fixed distance from each other, and the data processing assembly further comprises a setting unit for setting a standard value of intensity of gamma-radiation, a further setting unit for setting a standard Lamb wave amplitude two substraction circuits, and a dividing circuit, outputs of the setting units being connected respectively to outputs of substraction circuits having their outputs connected to inputs of the dividing circuit and their inputs to outputs of the smoothing filters.

2. A device as claimed in claim 1, characterized by an additional pulse generator and an additional emitting ultrasonic converter having its input connected to an output of the additional pulse generator, the additional pulse generator having an input connected to the output of the one-shot multivibrator, and, wherein a storing vessel is hydraulically connected to the measuring vessel and has connections for feeding and draining the test medium, the storing vessel housing therein an additional emitting ultrasonic converter.

* * * * *